United States Patent [19]

Petit et al.

[11] Patent Number: 5,099,077
[45] Date of Patent: Mar. 24, 1992

[54] CHIRAL PHOSPHORUS COMPOUNDS, A PROCESS FOR THEIR MANUFACTURE AND THEIR APPLICATION TO THE CATALYSIS OF ENANTIOSELECTIVE SYNTHESIS REACTIONS

[75] Inventors: Michele Petit, Wasquehal; Andre Mortreux, Hem; Francis Petit, Wasquehal; Gerard Buono; Gilbert Peiffer, both of Marseille, all of France

[73] Assignee: Societe Chimique Des Charbonnages S.A., Paris, France

[21] Appl. No.: 398,539

[22] Filed: Oct. 11, 1989

Related U.S. Application Data

[60] Division of Ser. No. 107,919, Oct. 13, 1987, Pat. No. 4,877,908, which is a continuation of Ser. No. 698,412, Feb. 5, 1985, which is a continuation-in-part of Ser. No. 638,268, Aug. 6, 1984, abandoned.

[30] Foreign Application Priority Data

Aug. 5, 1983 [FR] France ................. 83 12953

[51] Int. Cl.$^5$ ............................................. C07C 211/00
[52] U.S. Cl. ....................................... 568/814; 564/452
[58] Field of Search ......................... 568/814; 564/452

[56] References Cited

PUBLICATIONS

Cesarotti et al., Gazzetta Chimica Italiana, vol. 117, #2, 1987, pp. 129-133.
Karim et al., J. Organomettallic Chemistry, vol. 317, 1986, pp. 93-104.

*Primary Examiner*—Jose G. Dees
*Assistant Examiner*—Deborah D. Carr
*Attorney, Agent, or Firm*—Finnegan, Henderson, Farabow, Garrett and Dunner

[57] ABSTRACT

A method of using a chiral phosphorus-containing ligands comprising at least one amine radical and at least one dihydrocarbylphosphioxy radical of the formula $W=OP(R)_2$; from the group consisting of:

those of the formula

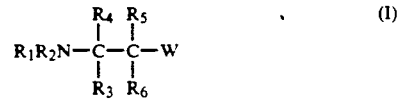

those of the formula

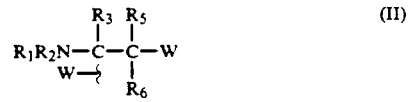

those of the formula

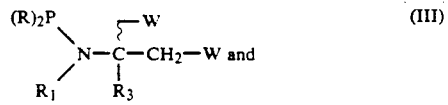

those of the formula

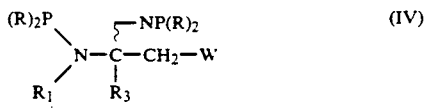

in a hydrogenation reaction for the synthesis of optically active organic compounds comprising reacting at least one organic compound that does not possess a center of asymmetry with (A), on the one hand, at least one transition metal complex of the formula $MZ_q$ in which M is a metal in group VIII of the Periodic Classification, q is the coordination number of the metal M, and Z is an atom or molecule capable of complexing the metal M and (B), on the other hand, at least one ligand L.

11 Claims, No Drawings

CHIRAL PHOSPHORUS COMPOUNDS, A PROCESS FOR THEIR MANUFACTURE AND THEIR APPLICATION TO THE CATALYSIS OF ENANTIOSELECTIVE SYNTHESIS REACTIONS

This is a division of application Ser. No. 07/107,919, filed Oct. 13, 1987 now U.S. Pat. No. 4,877,908 which is a continuation application of Ser. No. 06/698,412, filed Feb. 5, 1985, which is a continuation-in-part of application Ser. No. 06/638,268, filed Aug. 6, 1984, now abandoned.

FIELD OF THE INVENTION

The present invention relates to a novel family of novel chiral phosphorus-containing ligands, a process for their manufacture, and novel transition metal complexes incorporating these ligands, which are useful as catalysts in enantioselective synthesis reactions of organic compounds. The present invention relates also to methods for using chiral phosphorus-containing ligands such as enantioselective synthesis reactions of organic compounds, such as hydrogenation, hydroformylation, hydrosilylation, cyclodimerization and dimerization reactions. Among the hydrogenation reactions, the invention particularly concerns the manufacture of L-phenylalanine according to a process which allows to obtain, in a simple way, this product in a chemically and optically pure form.

BACKGROUND OF THE INVENTION

The industrial value of the synthesis of optically active substances, catalyzed by transition metal complexes containing chiral ligands, is well known. However, on account of the creation of at least one asymmetric center in an organic molecule, such catalytic reactions present great difficulty and are controlled industrially in only very special cases. Thus, it is known (U.S. Pat. Nos. 4,005,127, 4,142,992 and 4,220,590) that 3-(3,4-dihydroxyphenyl)alanine (L-DOPA) can be prepared by hydrogenation of 3-methoxy-4-acetoxyacetamidocinnamic acid with the aid of a homogeneous catalyst based on rhodium coordinated with a phosphorus ligand, followed by hydrolysis. However, the synthesis of this ligand requires a series of five stages, among them a separation of diastereoisomers, which consequently increases the overall prime cost of the procedure (B. D. VINEYARD, W. S. KNOWLES and M. J. SABACKY, Journal of Molecular Catalysis, 19 (1983) p. 161). It will be recalled that L-DOPA is used as the active principle in the treatment of Parkinson's disease. E. CESAROTTI, A. CHIESA and G. D'ALFONSO, in Tetrahedron Letters, Vol. 23, No. 29 (1982), pages 2995-96, have described the asymmetric hydrogenation, at 20° C. and under atmospheric pressure, of α-N-acetaminoacrylic acid, α-N-acetaminocinnamic acid, and itaconic acid in the presence of a cationic complex of the formula Rh(COD)L ClO4, in which COD denotes cyclooctadiene and L denotes the ligand N-(diphenylphosphino)-2-diphenylphosphinoxymethyl)pyrrolidine. E. CESAROTTI, A. CHIESA et al. have further described, in Journal Of Organometallic Chemistry, Vol. 251 (1983), pages 79-91, the asymmetric hydrogenation of α-N-acetaminocinnamic acid in the same conditions as above. However the optical yield in N-acetyl-(S)-phenylalanine that is obtained under such conditions is limited to 78% and the difficult problem of separating diastereoisomers is again encountered.

SUMMARY OF THE INVENTION

An object of the present invention therefore is chiral phosphorus-containing ligands that can be manufactured by a simple, low-cost process, and are capable of entering into the formation of transition metal complexes that can be used as catalysts in various enantioselective synthesis reactions of organic compounds.

Another and particular object of the present invention is a method of using chiral phosphorus-containing ligands in the synthesis reaction of chemically and optically pure L-phenylalanine.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention comprises a family of chiral phosphorus-containing ligands, such ligands comprising at least one amine radical and at least one dihydrocarbyl-phosphinoxy radical of the formula $W=OP(R)_2$, in which R is a hydrocarbon radical selected from the group consisting of alkyl, aryl, and cycloalkyl radicals, wherein the ligand is selected from the group consisting of:

those of the formula

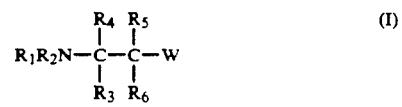

those of the formula

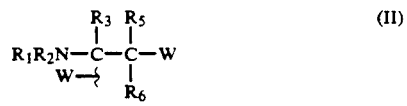

those of the formula

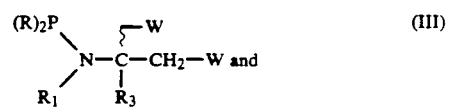

and those of the formula

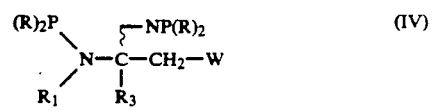

in which formulae:

$R_1$ and $R_2$ are selected from the group consisting of a hydrogen atom and hydrocarbon radicals;

$R_3$ and $R_4$, which must be different from one another, are selected from the group consisting of a hydrogen atom and hydrocarbon radicals that may or may not carry at least one functional group selected from the group consisting of the alcohol, thiol, thioether, amine, imine, acid, ester, amide, and ether functional groups; and $R_5$ and $R_6$ are selected from the group consisting of hydrogen atoms and hydrocarbon radicals that may or may not contain functional groups.

Further to achieve the foregoing objects and in accordance with the purpose of the invention, as embodied and broadly described herein, the invention comprises a process for the manufacture of the aforementioned chiral phosphorus-containing ligands comprising reacting, in a hydrocarbon solvent at a temperature of between $-50°$ and $80°$ C. and under an inert gas atmosphere, an optically active aminoalcohol of the general formula

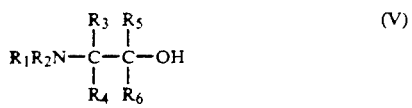

with at least one compound of the formula $P(R)_2Y$, wherein Y is selected from the group consisting of halogen atoms and amine radicals, the compound being present in a molar ratio, relative to the amino alcohol, that is greater than or equal to the number of $P(R)_2$ groups to be introduced into the chiral molecule.

Still further to achieve the foregoing objects and in accordance with the purpose of the invention, as embodied and broadly described herein, the invention comprises a method of using the aforementioned chiral phosphorus-containing ligand in a reaction for the enantioselective synthesis of organic compounds, comprising reacting one or more organic compounds that do not possess a center of asymmetry with (A) one or more transition metal complexes of the formula $MZ_q$, wherein M is a metal of group VIII of the Periodic Table, q is the degree of coordination of the metal M, and Z is an atom or molecule capable of complexing the metal M and (B) one or more such chiral phosphorus-containing ligands.

In a preferred embodiment, the invention comprises a method of using an aminophosphine-phosphinite chiral ligand of the formula

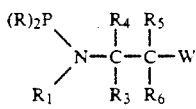

wherein:
R is a hydrocarbon radical selected from the group consisting of alkyl, aryl, and cycloalkyl radicals;
$R_1$ is selected from the group consisting of a hydrogen atom and hydrocarbon radicals;
$R_3$ and $R_4$, which must be different from one another, are selected from the group consisting of a hydrogen atom and hydrocarbon radicals that may or may not carry at least one functional group selected from the group consisting of the alcohol, thiol, thioether, amine, imine, acid, ester, amide, and ether functional groups; and
$R_5$ and $R_6$ are selected from the group consisting of a hydrogen atom and hydrocarbon radicals that may or may not contain functional groups, in a reaction for the enantioselective synthesis of organic compounds, comprising reacting one or more organic compounds that do not possess a center of asymmetry with (A) one or more transition metal complexes of the formula $MZ_q$, wherein M is a metal of group VIII of the Periodic Table, q is the degree of coordination of the metal M, and Z is an atom or molecule capable of complexing the metal M, and (B) one or more such chiral ligands, wherein the enantioselective synthesis reaction is selected from the group consisting of the hydrogenation and hydroformylation reactions of unsaturated organic substrates, the hydrosilylation reaction of ketones or imines, the cyclodimerization and dimerization reactions of conjugated dienes and the codimerization reactions of ethylene and a conjugated diene.

Still further to achieve the foregoing objects and in accordance with the purpose of the invention, as embodied and broadly described herein, the invention comprises a transition metal complex used as an intermediate in the aforementioned method of using a chiral phosphorus-containing ligand according to the invention, the complex being selected from the group consisting of those of the formula $MZ_{q-r}L_r$ and those of the formula $(MZ_{q-r}L_r) + A^-$, in which formulae r is 1 or 2 and L is the chiral phosphorus-containing ligand.

DESCRIPTION OF THE PREFERRED EMBODIMENTS

The first subject of the present invention is a family of novel chiral phosphorus-containing ligands comprising at least one amine radical and at least one dihydrocarbyl-phosphinoxy radical of the formula $W=OP(R)_2$, in which R is a hydrocarbon radical selected from the group consisting of alkyl, aryl, and cycloalkyl radicals, wherein the ligand is selected from the group consisting of:

those of the formula

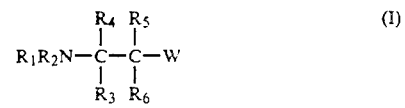

those of the formula

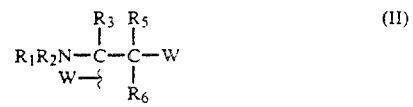

those of the formula

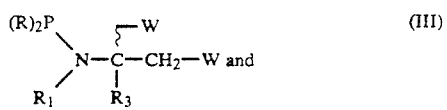

and those of the formula

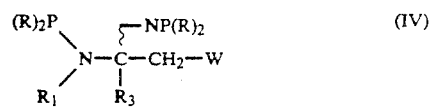

in which formulae:
$R_1$ and $R_2$ are selected from the group consisting of a hydrogen atom and hydrocarbon radicals;
$R_3$ and $R_4$, which must be different from one another, are selected from the group consisting of a hydrogen atom and hydrocarbon radicals that may or may not carry at least one functional group selected from the group consisting of the alcohol. thio, thioether, amine, imine, acid, ester, amide, and ether functional groups; and $R_5$ and $R_6$ are selected from the group consisting of hydrogen atoms and hydrocarbon radicals that may or may not contain functional groups.

The family of the ligands according to the invention can be classified into three sub-families according to the number of dihydrocarbylphosphine radicals present and according to their place in the molecule:

1) The sub-family or essentially monodentate chelates of formula (I) which will be named hereinafter "aminophosphinites".
2) The sub-family of essentially bidentate chelates of formula II, which will be named hereinafter "aminodiphosphinites".
3) The sub-family of essentially tridentate chelates comprises, on the one hand, the aminophosphinediphosphinites of general formula III, and, on the other hand, the diaminophosphinephosphinites of general formula IV.

In each of the formulae (I) to (IV), the radical R is, among others, selected from the methyl, ethyl, isopropyl, tertiobutyl, cyclohexyl and phenyl radicals.

In each of the formulae (I) to (IV), $R_1$ and $R_2$ are chosen from among a hydrogen atom and hydrocarbon radicals (the most frequent example of the latter is a methyl radical).

$R_3$ and $R_4$ must be different from one another and are selected from hydrogen and hydrocarbon radicals that may or may not carry at least one functional group selected from the group consisting of the alcohol, thiol, thioether, amine, imine, acid, ester, amide, and ether functional groups. Examples of radicals $R_3$ and $R_4$ are, in particular, the methyl, isopropyl, isobutyl, isoamyl, n-hydroxyethyl, isohydroxyethyl, n-aminobutyl, 4-methyleneimidazolyl, N-(n-propyl)guanidyl, ethanoyl, acetamidoyl, n-propionyl, n-propionamidoyl, benzyl, p-hydroxybenzyl, 3-methyleneindolyl, methanethioyl radicals, and the like.

The chiral phosphorus-containing ligands according to the invention are identified using their proton-, carbon 13- and phosphorus-31-nuclear magnetic resonance spectra, as well as their specified rotatory power.

Table I below summarizes the identification data of some aminophosphinephosphinites, in which R is the phenyl radical, according to the amino alcohol or amino acid from which they are derived.

Table II below summarizes the identification data of some aminophosphinites, in which R is the phenyl radical, according to the amino alcohol or amino acid from which they are derived.

Table III below summarizes the identification data of some aminophosphinediphosphinites and, as regards the ligand issuing from tryptophane, of a diaminophosphine-phosphinite in which R is phenyl radical.

In these tables, $(\alpha)_D^{25}$ designates the specific rotatory power at 25° C. expressed in degrees for the D-Ray, and $\delta$ designates the chemical shift expressed in ppm relative to phosphoric acid (in the case of phosphorus-31) or tetramethylsilane (in the case of proton and carbon-13). The notations (m), (dd), (d), and (s) designate respectively a multiplet, double doublet, doublet and singlet.

TABLE I

| Ligand No. | aminoalcohol or aminoacid precursor | Ligand name | 31 δP | 13 δC | 1 δH | $[\alpha]_D^{25}$ |
|---|---|---|---|---|---|---|
| 1 | erythro (+) Ephedrine | (1R,2S)-1-phenyl-1-(oxydiphenylphosphino)-2-(N-methyl-N diphenylphosphine amino)-2-methyl ethane | 111,1 63,8 | 129–134(m) 86,9(dd) 65,8(dd) 31,8(d) 17,1(d) | 7–8 4,8 4,0 2,2 1.3 | −60,5 |
| 2 | threo (−) Ephedrine | (1R,2R)-1-phenyl-1-(oxydiphenylphosphino)-2-(N-methyl-N diphenylphosphine amino)-2-methyl ethane | 110,5 63,7 | 129–130(m) 86,8(dd) 66,2(dd) 31,0(d) 16,6(d) | 7–8 4,95 4,0 2,3 1,15 | −16,1 |
| 3 | Carbethoxyhydroxy-proline | (2S,4R)-N-diphenylphosphino-2-carbethoxy-4-(oxydiphenyl-phosphino)-pyrrolidine | 108,4 46,3 | | | −96,2 |
| 4 (a) | Prolinol | N-dicyclohexylphosphino-2-(oxymethylene dicyclohexylphos-phino)pyrrolidine | 146,5 53,9 | 74,9(m) 64,4(dd) 47,2(d) 23–30(m) 24,4(s) | | −37,4 |
| 5 | Prolinol (+) | (S)N-diphenylphosphino-2-(oxymethylene diphenylphosphino)-pyrrolidine | 113,5 45,6 | 128–133(m) 73,1(dd) 63,8(dd) 47,2(d) 29,6(d) 25,4(s) | 7,1–8 3,3–4 3,05 2,07 1,5–2,1 | +22,6 (b) |
| 6 | Phenyglycine D (−) | (S)-1-(oxydiphenylphosphino)-2-(N-methyl-N-diphenyl-phosphine amino)-2-phenyl ethane | 114,9 59,3 | 127–133(m) 69,5(dd) 68,7(dd) 33,4(d) | 7,2 4,3 4,2 2,3 | −3,7 |
| 7 | Alanine | (S)-1-(oxydiphenylphosphino)-2-(N-methyl-N-diphenyl-phosphine amino)-2-methyl ethane | 113,2 58,1 | 125–136(m) 72,6(dd) 61,0(dd) 32,5(d) 16,8(d) | | +23,7 |
| 8 | Valine | (S)-1-(oxydiphenylphosphino)-2-(N-methyl-N-diphenyl-phosphine amino)-2-isopropyl ethane | 114,3 62,0 | 127–134(m) 73,1(dd) 71,1(dd) 33,5(d) 29,0 21,35 21,3 | | +4,4 |
| 9 | Leucine | (S)-1-(oxydiphenylphosphino)-2-(N-methyl-N-diphenyl- | 113,8 | 126–142(m) | | +15,4 |

TABLE I-continued

| Ligand No | aminoalcohol or aminoacid precursor | Ligand name | 31 δP | 13 δC | 1 δH | $[\alpha]_D^{25}$ |
|---|---|---|---|---|---|---|
| | | phosphine amino)-2-isobutyl ethane | 59,5 | 72,2(dd) 64,0(dd) 39,8(d) 32,2(d) 24,6 23,5 21,9 | | |
| 10 | Phenylalanine | (S)-1-(oxydiphenylphosphino)-2-(N-methyl-N diphenyl-phosphine amino)-2-benzyl ethane | 114,2 60,0 | 126-140(m) 71,7(dd) 66,8(dd) 37,5(d) 32,7(d) | | +1,1 |

(a) in this ligand, R is cyclohexyl radical
(b) data obtained for 402 nm line instead of D-line

TABLE II

| Ligand No. | aminoalcohol or aminoacid precursor | Ligand name | 31 δP | 13 δC | 1 δH | | $[\alpha]_D^{25}$ |
|---|---|---|---|---|---|---|---|
| 11 | erythro (+) Ephedrine | (1R,2S)-1-phenyl-1-(oxydiphenylphosphino)-2-(N-methylamino)-2-methyl ethane | 112,3 | 127-132(m) 84,5(d) 61,1(d) 31,8(s) 15,2(s) | 0,92-1,03 1,59 2,23 2,82 4,78-5,01 7,27 | (d)(3H) (s)(1H) (m)(3H) (m)(1H) (m)(1H) (m)(10H) | |
| 12 | Valine | (S)-1-(oxydiphenylphosphino)-2-(N-methylamino)-2-isopropyl ethane | 113,7 | 127-135(m) 69,2(d) 65,9(d) 34,5 29,3 18,9 18,8 | | | +25,9 |
| 13 | Prolinol | (S)-2-(oxymethylene diphenylphosphino)pyrrolidine | 113,1 | | 1,69 2,85 3,20 3,64-3,87 7,4 | (m)(5H) (m)(2H) (m)(1H) (m)(2H) (m)(10H) | |
| 14 | Glycine | (S)-1-(oxydiphenylphosphino)-2-(N-methylamino) ethane | 113,5 | | 1,31 2,30 2,73 3,80-3,97 7,14-7,48 | (s)(1H) (s)(3H) (t)(2H) (t-d)(2H) (m)(10H) | |

TABLE II

| Ligand No. | aminoalcohol or aminoacid precursor | Ligand name | 31 δP | $[\alpha]_D^{25}$ |
|---|---|---|---|---|
| 25 | glutamic acid | (S)-1,5-bis(oxydiphenylphosphino)-2-(N-methyl-N-diphenylamino)pentane | 113,8(s) 111,0(s) 58,6(s) | +1,4 |
| 16 | Asparagine | (S)-1,4-bis(oxydiphenylphosphino)-2-(N-methyl-N-diphenylamino)butane | 114,0(s) 111,7(s) 57,5(s) | −11,5 |
| 17 | Threonine | (2S,3R)-1,3-bis(oxydiphenylphosphino)-2-(N-methyl-N-diphenylamino) butane | 114,0(s) 111,5(s) 64,6(s) | +13,8 |
| 18 | Tryptophane | (S)N,N'-bisdiphenylphosphino-2-(methylamino)-1-(oxydiphenylphosphino)-3-(3-indolyl)propane | 113,5(s) 59,1(s) 16,8(s) | −5,5 |

A second subject of the present invention is a process for manufacturing the novel chiral phosphorus-containing ligands described above. The process according to the invention comprises reacting an optically active amino alcohol of general formula

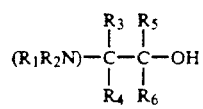

(V)

in which:
R$_5$ and R$_6$ have the meaning set forth above,

R$_1$ and R$_2$, which can be identical or different, are chosen from among a hydrogen atom and hydrocarbon radicals, and R$_3$ and R$_4$, which are necessarily different, are chosen from among a hydrogen atom and hydrocarbon radicals optionally bearing at least one functional group chosen from among the alcohol, thiol, thioether, amine, imine, acid, ester, amide, and ether functional groups, in a hydrocarbon solvent at a temperature between −50° C. and 80° C. and under an inert gas atmosphere, with at least one compound of formula P(R)$_2$Y, in which Y is chosen from among the halogen atoms and amine radicals, the compound being present in a molar ratio, relative to the amino alcohol, greater than or equal to the number of P(R)$_2$ groups to be introduced into the chiral molecule.

For the synthesis of the ligands of formulae (I) and (II), it is preferable to use a compound in which Y is an amine radical. For the synthesis of the ligands of formulae (III) and (IV), it is preferable to use a compound in which Y is a halogen atom. By hydrocarbon solvent in the sense of the present invention, there is understood, for example, benzene, toluene, and the like. To facilitate the elimination of the hydrochloric acid formed in the reaction, the latter can advantageously be performed in the presence of an excess of tertiary amine, such as, for example, triethylamine, which will precipitate in the form of hydrochloride. The chiral phosphorus-containing ligand is isolated successively by filtration of the precipitate followed by evaporation of the hydrocarbon solvent under vacuum. It generally appears in the form of a viscous oil. The chiral amino alcohols of formula (V) are most often either commercial products or products that are readily accessible by reduction of natural amino acids (or their formylated methyl esters). When the radical R$_3$ or R$_4$ of the amino alcohol of formula (V) bears a functional group, the latter can be introduced by a well known functionalization reaction; for example, the ester function will be introduced by esterification of the corresponding acid function(in the case of the carbalkoxyhydroxyprolines). By way of examples, there may be mentioned prolinol, hydroxyproline, the ephedrines, and the N-methyl amino alcohols derived from the following natural amino acids: glycine, phenylglycine, phenylalanine, leucine, serine, threonine, histidine, lysine, arginine, isoleucine, valine, alanine, tyrosine, tryptophane, methionine, cysteine, glutamine, asparagine, aspartic acid, glutamic acid, cystine, and the like.

In a preferred embodiment, the invention comprises a method of using an aminophosphine-phosphinite chiral ligand of the formula

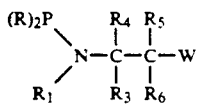

wherein W, R, R$_1$, R$_3$, R$_4$, R$_5$ and R$_6$ have the same meaning as above. Some of the ligands of this family have not been described in the prior art previously cited. They can be manufactured according to the same process as above which comprises reacting, in a hydrocarbon solvent, at a temperature of between $-50°$ and $+80°$ C., under an atmosphere of inert gas, one optically active aminoalcohol (V) with at least one compound of formula P(R)$_2$Y. The optically active aminoalcohol is selected from prolinol, hydroxyproline, ephedrines and the N-methylated aminoalcohols derived from the following natural aminoacids: phenylglycine, phenylalanine, leucine, valine, alanine. In this particular embodiment, Y is selected from the group consisting of amine radical and halogen atoms; preferably halogen atoms are used, and the molar ratio of the compound relative to the aminoalcohol is greater than or equal to 2. The elimination of the hydrochloric acid formed and the isolation of the chiral phosphorus-containing ligand are performed as described hereabove for the ligands of formulae (I) to (IV).

A third subject of the present invention relates to the application of the novel chiral phosphorus-containing ligands described above to enantioselective synthesis reactions of organic compounds. This application comprises reacting at least one organic compound that does not possess a center of asymmetry with (A), on the one hand, at least one transition metal complex of formula MZq in which M is a metal in group VIII of the Periodic Classification, q is the coordination number of the metal M, and Z is an atom or molecule capable of complexing the metal M and (B), on the other hand, at least one chiral phosphorus-containing ligand as described above. If required, the reaction, can be performed in the presence of (C) at least one agent capable of capturing at least one ligand Z of the constituent (A). This agent (C) can be either an acid possessing an anion A$^-$ that is weakly coordinating and sterically hindered or a metal salt of such an acid, or it can be quantity of electricity introduced by electrolysis at a prescribed cathodic potential. By an anion A$^-$ that is weakly coordinating and sterically hindered, there is understood especially the perchlorate, tetrafluoro- and tetraphenylborate, and hexafluorophosphate anions. The metal salts that can be used are mainly those of silver and thallium.

On the other hand, the enantioselective synthesis reaction can be carried out, if required, in the presence of (D) at least one activator chosen from among the aluminum derivatives of formula AlR$_n$X$_{3-n}$, in which $0 \leq n \leq 3$, X is a halogen atom, and R is an alkyl radical having from 1 to 12 carbon atoms. The constituents (A) and (B) are generally in a molar ratio (B)/(A) of between 1 and 10. The constituents (A) and (D) are generally in a molar ratio (D)/(A) of between 0.1 and 10. The constituent (A) and the agent (C) are generally in a molar ratio (C)/(A) less than or equal to q, when (C) is an acid or salt.

Among the metals M that can generally be used, there may be mentioned iron, nickel, cobalt, rhodium, ruthenium, iridium, palladium, and platinum. Among the atoms or molecules Z that can generally be used, there may be mentioned carbon monoxide, the halogens, ethylene, norbornadiene, cyclooctadiene, and acetylacetone. Finally, the coordination number q can generally be between 2 and 6 inclusive, according to the metal and/or the ligands used.

Any organic compound that does not possess a center of asymmetry can be subjected to an enantioselective synthesis reaction according to the invention. The same applies to some olefins, ketones, and dienes, optionally bearing a functional group or groups. Examples of reactions according to the invention are the following well-known reactions:

hydrogenation and hydroformylation of unsaturated organic substrates (such as alkenes optionally bearing a functional group in the α position to the double bond), particularly the dehydroaminoacids or their N-acetylated derivatives such as the acetamidocarboxylic acids.

The hydrogenation reactions are generally carried out at a temperature between $-50°$ and $+200°$ C. and under a pressure between 1 and 200 bars, with, generally, an hydrogen amount in a stoichiometric ratio relative to the substrates. In a particular embodiment concerning the hydrogenation of acetamidocinnamic acid, it is preferred to use a process that consists of hydrogenating acetamidocinnamic acid in the presence of a complex of a metal M of the group VIII of the Periodic Table, in the presence of a solvent, under a pressure greater than or equal to atmospheric pressure, at a temperature from −50° C. to +10° C., for a time less than or equal to 300 minutes, the molar ratio of acetamidocinnamic acid to metal M being greater than or equal to 100, the complex of metal M being selected from, on the one hand, those having the formula $MZ_{q-r}L_r$ and, on the other hand, those having the formula $(MZ_{q-r}L_r)^+A^-$, in which r is equal to 1 or 2, q is the coordination number of the metal M, Z is an atom or a molecule capable of complexing the metal M, $A^-$ is an anion that is weakly coordinating and sterically hindered, and L is a chiral phosphorus-containing ligand selected from those belonging to the "aminophosphine-phosphinites" family whose formula is:

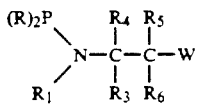

in which W, R, $R_1$, $R_3$, $R_4$, $R_5$ and $R_6$ have the same meaning as above.

The formation of the complexes of the metal M is described hereinafter.

The hydrogenation reaction of acetamidocinnamic acid allows to obtain, with a very good chemical yield, the N-acetyl-(S)-phenylalanine with an optical yield greater than or equal to 85%. Further, according to an embodiment of this particular process that consists in at least once recrystallizing in ethanol the product obtained after hydrogenation, it is possible to improve in a surprising manner the optical yield in N-acetyl-(S)-phenylalanine that can reach a value of 99%. The hydrolysis of N-acetyl-(S)-phenylalanine leads afterwards to L-phenylalanine.

The hydroformylation reactions are generally carried out at a temperature between 15° and 300° C. and under a pressure between 1 and 350 bars. These reactions can be industrially applied especially to the synthesis of sweeteners having no food-value such as aspartame and (R)6-methyltryptophane.

Reduction of prochiral ketones or imines with organosilanes, in particular monohydrosilanes and, preferably, dihydrosilanes (hydrosilylation reaction).

Cyclodimerization and dimerization of conjugated dienes, and codimerization of ethylene and a conjugated diene; these reactions are generally carried out at a temperature between −30° and +100° C. and under a pressure less than 100 bars.

A fourth subject of the present invention relates, by way of novel products used as intermediates in the application of the novel ligands to enantioselective synthesis reactions described above, to complexes of transition metals chosen on the one hand from those of formula $MZ_{q-r}L_r$, and on the other hand from those of the formula $(MZ_{q-r}L_r)^+A^-$, formulae in which M, Z, A, and q have the same meanings as described above, r is equal to 1 or 2, and L is the chiral phosphorus-containing ligand. These complexes are formed, in the scope of the application, by reaction between the complex of formula MZq on the one hand and the ligand L on the other hand, in the presence of at least one acid or salt possessing an anion $A^-$, if required.

These transition metal complexes are identified with the aid of their phosphorus-31-nuclear magnetic resonance spectra. Table IV below summarized the identification data of some complexes of formula $[Rh(norbornadiene)L]^+ClO_4^-$, according to the nature of the ligand L.

TABLE IV

| Ligand No. | 1 | 2 | 3 | 5 | 6 |
|---|---|---|---|---|---|
| 31 | 120,9 | 122,4 | 110,4 | 122,8 | 110.7 |
| δP | 90,8 | 95,3 | 96.8 | 71,5 | 85,5 |
| Ligand No. | 7 | 8 | 9 | 10 | 18 |
| 31 | 119,5 | 119,5 | 118,8 | 116,7 | 118,0 |
| δP | 87,3 | 88,8 | 87,8 | 88,5 | 88,3 |
|  |  |  |  |  | 33,6 |

The following examples are given by way of illustration and without limitation of the present invention.

EXAMPLE 1

2 moles of chlorodiphenylphosphine are reacted in dry benzene, at a temperature of +5° C. and under an atmosphere of nitrogen, with 1 mole of erythro-(+)-ephedrine (2-methylamino-1-phenyl-1-propanol) (made anhydrous by azeotropic distillation of the water with benzene) in the presence of an excess of triethylamine. The precipitate of triethylamine hydrochloride formed is filtered off, and the benzene is then evaporated under vacuum. A recrystallization carried out in benzene permits the removal of a by-product identified as methylaminobis(diphenylphosphine): proton-nuclear magnetic resonance analysis in fact reveals chemical shifts δ at 7.6 and 3.5 ppm relative to tetramethylsilane. 0.8 mole of ligand No. 1 (see Table I) is then obtained, of chemical purity estimated at 95%.

EXAMPLE 2

The synthesis procedure of Example 1 is repeated, replacing the erythro-(+)-epherine respectively by:

Threo-(−)-ephedrine, with a view to obtaining ligand No. 2.

(S)-(+)-Prolinol, with a view to obtaining ligand No. 5.

(R)-(−)-methylphenylglycinol, with a view to obtaining ligand No. 6.

-N-Methyl-2-aminopropanol, with a view to obtaining ligand No. 7.

The N-methylated alcohol derived from α-aminoisovaleric acid (valine), with a view to obtaining ligand No. 8.

The N-methylated alcohol derived from 2-amino-4-methyl-n-valeric acid (leucine), with a view to obtaining ligand No. 9.

N-Methyl-2-amino-3-phenylpropanol, with a view to obtaining ligand No. 10.

Carbethoxyhydroxyprolinol, with a view to obtaining ligand No. 3.

These ligands, the identification data of which appear in Table I above, are obtained in identical or similar yield to that of Example 1.

By way of reminder, it will be recalled that (S)-(+)-prolinol can be readily obtained by reduction of 2-pyrrolidinecarboxylic acid (proline) by means of the double lithium aluminum hydride, LiAlH$_4$, suspended in tetrahydrofuran. Likewise, the other amino alcohols are prepared from the corresponding natural amino acids by monoformylation of the amine function, esterification of the acid function and then reduction by LiAlH$_4$.

EXAMPLE 3

The synthesis procedure of Example 1 is repeated replacing. on the one hand, erythro-(+)-ephedrine by S(+)prolinol and, on the other hand, chlorodiphenylphosphine by chlorodicyclohexylphosphine.

Ligand No. 4 (see Table I above) is then obtained with the same yield.

EXAMPLE 4

1 mole of dimethylaminodiphenylphosphine is reacted in dry benzene under an atmosphere of nitrogen with 1 mole of erythro-(+)-ephedrine (made anhydrous by azeotropic distillation of the water with benzene). After liberation of the dimethylamine, the benzene is evaporated under vacuum and 0.8 mole of ligand No. 11 (see Table II above) is recovered, of chemical purity estimated at 90%.

EXAMPLE 5

The synthesis procedure of Example 4 is repeated, replacing the erythro-(+)-ephedrine successively by:
The N-methylated alcohol derived from α-aminoisovaleric acid (valine), to obtain ligand No. 12 (see Table II).
The N-dimethylated alcohol derived from valine, to obtain(S)-1-(oxydiphenylphosphino)-2-(N-dimethylamino)-2-isopropylethane identified as follows: $31_p = 112.7$ (s).

These ligands are obtained in similar or identical yield to that of Example 4.

EXAMPLE 6

3 moles of chlorodiphenylphosphine are reacted in dry benzene under an atmosphere of nitrogen with 1 mole of the N-methylated alcohol derived from glutamic acid, in the presence of an excess of triethylamine. The precipitate of triethylaminehydrochloride formed is filtered off and benzene is then evaporated under vacuum. 0.8 mole of ligand No. 15 (see Table III above) is then obtained, of chemical purity estimated at 85%.

EXAMPLE 7

The synthesis procedure of Example 6 is repeated, using as amino alcohols the N-methylated alcohols derived from:
Aminosuccinic acid (asparagine), to obtain ligand No. 16.
2-Amino-3-hydroxybutyric acid (threonine), to obtain ligand No. 17.
2-Amino-3-(3-indolyl)propionic acid (tryptophane), to obtain ligand No. 18.

These ligands are obtained in identical or similar yield to that of Example 6.

EXAMPLE 8

1 mole of the ligand No. 1 (hereafter named "L") and 0.5 mole of dichlorotetracarbonyldirhodium are reacted in dry benzene at a temperature of 20° C. The solvent is evaporated and then, after washing with a petroleum ether and drying under vacuum, 0.8 mole of a complex of formula RhCl(CO)L is recovered. This complex is identified by its phosphorus-31-nuclear magnetic resonance spectrum, which shows chemical shifts at 90.1 ppm (dd); 99.7 ppm (dd); 111.6 ppm (dd) and 128.7 ppm (dd).

EXAMPLE 9

Asymmetric Hydroformylation

10 $cm^3$ of anhydrous benzene and 40 $cm^3$ of freshly distilled propylene carbonate are added successively to 0.1 millimole of the complex of Example 8. The dissolution is accomplished under nitrogen and the solution is introduced under an inert gas into a 320 $cm^3$ electrochemical autoclave equipped with three electrodes; a platinum electrode (cathode), an iron electrode (anode) and a reference electrode enabling a liquid junction to be established between the inside of the autoclave and the external atmospheric pressure. This latter electrode consists of a tube pierced in its center, into which an asbestos wick is introduced. The latter soaks up solvent liquid and a gland system enables the wick to be compressed and the internal pressure to be counteracted, while permitting a slight flow of liquid to be passed to effect a junction with a saturated calomel electrode situated outside the autoclave. This three-electrode assembly is necessary to perform a reduction at a prescribed cathodic potential, with the aid of a potentiostat. 4.5 g of freshly distilled styrene is then added. The reactor is then charged with a $CO/H_2$ (1:1) mixture at a temperature of 25° C. under 10 atmospheres. The solution is electrolyzed at a cathodic reduction potential of −0.9 volts, until the current intensity becomes less than 5% of its maximal value, this corresponding to approximately 1 faraday per gram-atom of rhodium (reduction time=approximately 4 hours). Gas chromatography permits determination of the degree of conversion, 45% of the styrene being converted, in molar terms, into a mixture consisting of 93% of 2-phenylpropanal and 7% of 3-phenylpropanal. The benzene is removed from the reaction mixture by evaporation under vacuum and rectification of the products is then carried out under vacuum. A solution of aldehydes in propylene carbonate is thus obtained, freed of the presence of the metal complex, and the measurement of rotatory power is carried out directly on this solution: the optical yield is 25% of aldehyde with S-configuration.

EXAMPLE 10

Asymmetric Cyclodimerization 687 mg (2.5 millimoles) of bis(1,5-cyclooctadiene)-nickel and then 947.5 mg (2.5 millimoles) of the ligand No. 9 are introduced successively into a glass tube.

These compounds are solubilized in 2 g of heptane and approximately 15 $cm^3$ of toluene, so as to obtain a concentration of catalyst of 0.1 mole per liter after addition of 6.75 g (0.13 mole) of 1,3-butadiene by bubbling it into the solution maintained at 0° C. The reaction mixture is then maintained stirred at a temperature of 40° C. for 24 hours. The reaction pressure reaches approximately 5 bars. At the end of the reaction, the catalysate is filtered on silica to remove the catalyst and the clear solution obtained is distilled on a column to separate the 4-vinylcyclohexene from its 1,5-cyclooctadiene isomer, which is liberated from the initial catalyst and formed during the reaction. In fact, a mixture consisting essentially of 40% of 1,5-cyclooctadiene and 52% of 4-vinylcyclohexene is obtained in a chemical yield of 85%. The 4-vinylcyclohexene is obtained with an optical purity of 25%.

EXAMPLE 11

Asymmetric Hydrogenation

In a Schlenk tube and under nitrogen, 0.1 millimole of Cramer complex $Rh_2Cl_2(C_2H_4)_4$ is dissolved in 8 cm$^3$ of 95% strength ethanol, a solution of 0.2 millimole of the ligand No. 3 in 12 cm$^3$ of 95% strength ethanol is added by means of a transfer tube, and the mixture is stirred for 15 minutes under nitrogen at 20° C. The complex thus obtained, of formula RhLCl, is transferred under hydrogen intro a previously purged reactor containing 0.01 mole of acetamidoacrylic acid dissolved in 40 cm$^3$ of 95% strength ethanol. Hydrogen is introduced into the reactor and the reaction, which is carried out at 20° C. at atmospheric pressure, is followed by reading the volume of hydrogen absorbed. After 1 hour of reaction, the ethanol is evaporated off, the residue is taken up in hot water and the mixture is then filtered to separate the insoluble complex. The water is evaporated off and N-acetylalanine is then recovered, in a chemical yield of 98%. Its specific rotatory power, measured on an aqueous solution of concentration 2 g/100 cm$^3$, corresponds to an optical yield of 73.5% ($[\alpha_D^{25}] = +48.9°$).

EXAMPLE 12

The procedure described in Example 11 is repeated replacing the ligand No. 3 by the ligand No. 4.

N-acetylalanine is recovered with the same chemical yield. Its specific rotatory power $(\alpha)_D^{25} = +48.5°$ corresponds to an optical yield of 73%.

EXAMPLE 13

Asymmetric Hydrosilylation

In a Schlenk tube and under nitrogen, 0.2 millimole of Cramer complex $Rh_2Cl_2(C_2H_4)_4$ is dissolved in 10 cm$^3$ of benzene, a solution of 0.4 millimole of the ligand No. 3 in 10 cm$^3$ of benzene is added by means of a transfer tube, and the mixture is stirred for 15 minutes under nitrogen at 20° C. The complex thus obtained, of formula RhLCl, is transferred under nitrogen into a previously purged reactor containing 2.34 cm$^3$ of acetophenone (0.02 mole), 4.1 cm$^3$ of α-naphtylphenylsilane (0.02 mole) and 30 cm$^3$ of benzene. The reaction is continued for 4 hours at 20° C. and atmospheric pressure. The benzene is then evaporated off under vacuum. The residue is dissolved in 60 ml of acetone containing 12 ml of an aqueous 10% strength hydrochloric acid solution, and the mixture is stirred for 2 hours. The organic phase is extracted with ether and the extract is neutralized with a 5% strength sodium carbonate solution and then with distilled water. The ether phase is then dried over MgSO$_4$, filtered and evaporated under vacuum. After distillation, 1-phenylethanol is recovered, in a chemical yield of 96%. Its specific rotatory power $(\alpha)_D^{25} = -22.4°$ corresponds to an optical yield of 42.6%.

EXAMPLE 14

The procedure described in Example 13 is repeated replacing the ligand No. 3 by ligand No. 8 and α-naphtylphenylsilane by diphenylsilane. 1-phenylethanol is again obtained in a chemical yield of 96% and an optical yield of 26%.

EXAMPLE 15

Asymmetric Codimerization 110 mg (0.4 millimole) of bis(1,5-cyclooctadiene)-nickel, 33 cm$^3$ of anhydrous toluene, 2 g of heptane, 220 mg (0.4 millimole) of the ligand No. 17, 0.2 g (1.6 millimole) of diethylaluminum chloride, and then 4 g (0.05 mole) of 1,3-cyclohexadiene are introduced successively into a 300 cm$^3$ autoclave previously purged with nitrogen. The autoclave is then closed, after which it is charged with ethylene until a quantity is reached which is equimolar with that of the diene. The reaction is then continued with stirring for 15 minutes at −30° C. and under a pressure of 6 bars. After rectification, (S)-3-vinylcyclohexene is obtained at 97% purity in a chemical yield of 80%, and possessing a specific rotatory power, $(\alpha)_D^{25} = 245°$, equivalent to an optical yield of 92.3%.

EXAMPLE 16

Synthesis of $[Rh(norbornadiene)L]^+ClO_4^-$ a) First Method

A solution of 120 mg of 70% strength perchloric acid in 2 cm$^3$ of tetrahydrofuran is added under nitrogen and at 20° C. to 0.85 millimole of complex Rh(norbornadiene)(acetylacetonate) and to 1 millimole of ligand L which is dissolved in 3 cm$^3$ of tetrahydrofuran. As soon as the color of the solution becomes orange, crystals appear. The phenomenon is enhanced by addition of ethyl ether. The mixture is filtered under nitrogen and the crystals are washed with methanol and then ethanol, and then dried under vacuum. The ionic complex $[Rh(norbornadiene)L]^+ClO_4^-$ is thus recovered, in better than 80% yield.

b) Second Method 1.1 millimole of silver perchlorate is added under nitrogen and at 20° C. to 1 millimole of complex $Rh_2(norbornadiene)_2Cl_2$ dissolved in 50 cm$^3$ of methanol containing 1 millimole of ligand L. After 15 minutes' stirring, the precipitate of silver chloride is filtered off. The filtrate is evaporated, washed with benzene under nitrogen and then with ethyl ether, and then dried under vacuum. The crystals of the ionic complex $[Rh(norbornadiene)L]^+ClO_4^-$ are thus recovered, in better than 80% yield.

The phosphorus-31-nuclear magnetic resonance spectrum for the various complexes thus prepared enables them to be identified, according to the nature of ligand L (see Table IV above).

EXAMPLES 17 TO 19

Asymmetric Hydrogenation 0.1 millimole of an ionic complex prepared in accordance with Example 16, dissolved in 10 cm$^3$ of 95% strength ethanol, is transferred under hydrogen into a previously purged reactor containing 0.01 mole of acetamidoacrylic acid dissolved in 40 cm$^3$ of 95% strength ethanol. Hydrogen is introduced into the reactor and the reaction, which is carried out at 20° C. and atmospheric pressure, is followed by reading the volume of hydrogen absorbed. After 1 hour's reaction, the ethanol is evaporated off, and the residue is taken up in hot water and the solution then filtered to separate the insoluble complex. The water is evaporated off and N-acetylalanine is then recovered, in a chemical yield of 98%. Its specific rotatory power $(\alpha)_D^{25}$, measured on an aqueous solution of concentration 2 g/100 cm$^3$, is related to the optical yields (O.Y.) shown in Table V below according to the nature of the ligand L.

TABLE V

| Example | Ligand No. | $(\alpha)_D^{25}$ | O.Y. (%) |
|---------|-----------|-------------------|----------|
| 17      | 2         | 31.7              | 47.7     |
| 18      | 7         | 41.8              | 62.8     |
| 19      | 5         | 53.2              | 80.0     |

EXAMPLE 20

The procedure of Examples 17 to 19 is repeated using high-purity hydrogen and replacing 95% strength ethanol by pure ethanol, L being the ligand No. 3.

N-acetylalanine is then recovered, with the same chemical yield. Its specific rotatory power $(\alpha)_D^{25} = +56.6°$ corresponds to an optical yield of 85%.

EXAMPLES 21

The procedure of Example 19 is repeated replacing acetamidoacrylic acid by acetamidocinnamic acid.

(S)-N-acetylphenylalanine is recovered with an optical yield of 82%.

EXAMPLES 22 to 24

Into a previously purged reactor containing 0.1 mole of acetamidocinnamic acid dissolved in 400 cm$^3$ of 95% strength ethanol is transferred, under hydrogen, 0.5 millimole of ionic complex obtained according to example 16, second method, using ligand No. 5 instead of ligand No. 1, and dissolved into 50 cm$^3$ of 95% strength ethanol. Hydrogen is introduced into the reactor and the reaction is controlled by reading the absorbed hydrogen volume. For each example the temperature T (in °C.) and the duration t (in minutes) of the reaction are reported in Table VI below. At the end of the reaction, ethanol is evaporated, the residue is treated with hot water and then filtered to recover the insoluble complex. Water is evaporated from the filtrate and N-acetyl-(S)-phenylalanine is recovered, in a chemical yield of 98%. The measure of its specific rotatory power $(\alpha)_D^{25}$ on an aqueous solution at a concentration of 20 g/l permits the calculation of the optical yield (O.Y.) (expressed in %) shown in Table VI below, in function of the reaction conditions.

TABLE VI

| Example | T (°C.) | t   | O.Y. |
|---------|---------|-----|------|
| 22      | +10     | 35  | 86   |
| 23      | 0       | 40  | 95   |
| 24      | -20     | 120 | 89   |

EXAMPLES 25

The product coming from the hydrogenation reaction of Example 22 is recrystalized in ethanol providing a N-acetyl-(S)-phenylalanine with an optical yield of 99.4%.

It will be apparent to those skilled in the art that various modifications and variations could be made in the invention without departing from the scope or spirit of the invention.

What is claimed is:

1. A method of using a chiral phosphorus-containing ligand comprising at least one amine radical and at least one dihydrocarbylphosphinoxy radical of the formula W=OP(R)$_2$, in which R is a hydrocarbon radical selected from the group consisting of alkyl, aryl, and cycloalkyl radicals, wherein said ligand is selected from the group consisting of:
those of the formula $$R_1R_2N-\underset{\underset{R_3}{|}}{\overset{\overset{R_4}{|}}{C}}-\underset{\underset{R_6}{|}}{\overset{\overset{R_5}{|}}{C}}-W \quad (I)$$

those of the formula $$R_1R_2N-\underset{W-}{\overset{\overset{R_3}{|}}{C}}-\underset{R_6}{\overset{\overset{R_5}{|}}{C}}-W \quad (II)$$

those of the formula $$\begin{array}{c}(R)_2P\\\diagdown\\\phantom{(R)_2}N-C-CH_2-W\\\diagup\phantom{N}|\\R_1\phantom{N-}R_3\end{array} \quad \begin{array}{c}\phantom{N}-W\\\phantom{N}\end{array} \text{ and} \quad (III)$$

and those of the formula $$\begin{array}{c}(R)_2P\\\diagdown\\\phantom{(R)_2}N-C-CH_2-W\\\diagup\phantom{N}|\\R_1\phantom{N-}R_3\end{array} \quad \begin{array}{c}\phantom{N}-NP(R)_2\\\phantom{N}\end{array} \quad (IV)$$

in which formulae:
R$_1$ and R$_2$ are selected from the group consisting of a hydrogen atom and hydrocarbon radicals selected from the group consisting of alkyl, aryl, and cycloalkyl radicals;
R$_3$ and R$_4$, which must be different from one another, are selected from the group consisting of a hydrogen atom and hydrocarbon radicals selected from the group consisting of alkyl, aryl, and cycloalkyl radicals that may or may not carry at least one functional group selected from the group consisting of the alcohol, thiol, thioether, amine, imine, acid, ester, amide, and ether functional groups; and
R$_5$ and R$_6$ are selected from the group consisting of hydrogen atoms and hydrocarbon radicals selected from the group consisting of alkyl, aryl, and cycloalkyl radicals that may or may not contain functional groups;
in a hydrogenation reaction for the synthesis of optically active organic compounds, comprising reacting one or more unsaturated organic compounds that do not possess a center of asymmetry with (A) one or more transition metal complexes of the formula MZ$_q$, wherein M is a metal of group VIII of the Periodic Table, q is the degree of coordination of the metal M, and Z is an atom or molecule capable of complexing the metal M and (B) one or more of said chiral phosphorus-containing ligands, said hydrogenation reaction being carried out at temperature of between −50° and +200° C. and under a pressure of between 1 and 200 bars.

2. A method as claimed in claim 1, wherein the unsaturated organic compound is acetamidocinnamic acid and wherein the hydrogenation is carried out at a temperature of between −50° and +10° C.

3. A method as claimed in claim 2, wherein the chiral phosphoruscontaining ligand that is utilized is the (S)-N-diphenylphosphino-2-(oxymethylenediphenylphosphino)-pyrrolidine.

4. A method as claimed in claim 2, wherein the product coming from the hydrogenation is at least once recrystallized in ethanol.

5. A method of using an aminophosphine-phosphinite chiral ligand of the formula

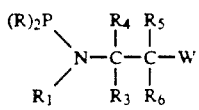

wherein:

W is $OP(R)_2$;

R is a hydrocarbon radical selected from the group consisting of alkyl, aryl and cycloalkyl radicals;

$R_1$ is selected from the group consisting of a hydrogen atom and hydrocarbon radicals selected from the group consisting of alkyl, aryl and cycloalkyl radicals;

$R_3$ and $R_4$, which must be different from one another, are selected from the group consisting of a hydrogen atom and hydrocarbon radicals selected from the group consisting of alkyl, aryl and cycloalkyl radicals that may or may not carry at least one functional group selected from the group consisting of the alcohol, thiol, thioether, amine, imine, acid, ester, amide, and ether functional groups; and $R_5$ and $R_6$ are selected from the group consisting of a hydrogen atom and hydrocarbon radicals selected from the group consisting of alkyl, aryl and cycloalkyl radicals that may or may not contain functional groups;

in a reaction of hydrogenation of acetamidocinnamic acid by reacting the acid with (A) one or more transition metal complexes of the formula $MZ_q$, wherein M is a metal of group VIII of the Periodic Table, q is the degree of coordination of the metal M, and Z is an atom or molecule capable of complexing the metal M and (B) one or more such chiral ligands, at a temperature of between $-50$ and $+10°$ C. and under a pressure between 1 and 200 bars.

6. A method as claimed in claim 5, wherein the aminophosphine-phosphinite chiral ligand that is utilized is the (S)-N-diphenylphosphino-2-(oxymethylenediphenylphosphino)-pyrrolidine.

7. A method as claimed in claim 5, wherein the product coming from the hydrogenation is at least once recrystallized in ethanol.

8. The method of claim 5, wherein the time of reaction is less than or equal to 300 minutes.

9. The method of claim 5, wherein the molar ratio of acetamidocinnamic acid to metal M is greater than or equal to 100.

10. The method of claim 5, wherein the amount of hydrogen used in the hydrogenation reaction is in a stoichiometric ratio relative to the acid.

11. The method of claim 5, wherein the transitional metal complex $MZ_q$ reacts with the aminophosphine-phosphinite chiral ligand to form either $MZ_{q-r}L_r$ or $(MZ_{q-r}L_r)^+A^-$, in which r is equal to 1 or 2, q is the coordination number of the metal M, Z is an atom or a molecule capable of complexing the metal M, $A^-$ is an anion that is weakly coordinating and sterically hindered, and L is the aminophosphine-phosphinite chiral ligand.

* * * * *